United States Patent [19]
D'Alfonso

[11] Patent Number: 6,166,538
[45] Date of Patent: Dec. 26, 2000

[54] AUTOCLAVE CYCLE MONITOR FOR AUTOCLAVED INSTRUMENTS

[75] Inventor: David A. D'Alfonso, Goleta, Calif.

[73] Assignee: Linvatec Corporation, Largo, Fla.

[21] Appl. No.: 09/141,010

[22] Filed: Aug. 26, 1998

[51] Int. Cl.[7] .......................... G01N 27/72; G01R 33/12; A61B 1/00
[52] U.S. Cl. .......................... 324/228; 324/219; 324/224; 324/235; 324/239; 324/261; 324/71.1; 422/119; 600/117
[58] Field of Search .................... 324/71.1, 71.2, 324/201, 202, 203, 209, 219, 224, 226, 228, 234, 235, 239, 260, 261, 262; 73/86, 768, 775, 779; 600/117, 133; 422/119; 702/34

[56] References Cited

U.S. PATENT DOCUMENTS

| | | |
|---|---|---|
| 3,450,489 | 6/1969 | Fay . |
| 3,568,627 | 3/1971 | Sellenger . |
| 3,833,339 | 9/1974 | Pacillio . |
| 3,872,448 | 3/1975 | Mitchell, Jr. . |
| 3,970,996 | 7/1976 | Yasaka et al. . |
| 4,130,881 | 12/1978 | Haessler et al. . |
| 4,235,842 | 11/1980 | Thomas et al. . |
| 4,449,518 | 5/1984 | Konomura et al. . |
| 4,514,361 | 4/1985 | Hirsch . |
| 4,596,150 | 6/1986 | Kuhr ................................ 324/209 X |
| 4,850,716 | 7/1989 | Baker et al. . |
| 5,057,433 | 10/1991 | Douglas . |
| 5,313,935 | 5/1994 | Kortenbach et al. . |
| 5,359,993 | 11/1994 | Slater et al. . |
| 5,654,511 | 8/1997 | Sugino et al. ................... 324/209 X |
| 5,830,121 | 11/1998 | Enomoto et al. ................ 600/117 |
| 5,939,641 | 8/1999 | Lotfi et al. ....................... 73/768 |

*Primary Examiner*—Gerard Strecker
*Attorney, Agent, or Firm*—Larson & Larson, P.A.; James E. Larson

[57] ABSTRACT

An electronic autoclave cycle passively records the number of thermal cycles to which an instrument has been subjected in a steam autoclave. When a sterilization cycle has been completed, and the instrument is next energized in use, a microprocessor is employed to read the sensor and record the occurrence of a sterilization cycle. Information as to the cumulative number of cycles through which the instrument has been subjected is stored in a non-volatile memory. This data is suitably displayed on a display panel. The sensor employed uses either the Curie temperature or a temperature near but below the Curie temperature of a ferromagnetic material by first magnetizing the material and then, later, checking its flux density to determine whether a thermal cycle has occurred. In a first embodiment, a Hall effect sensor is used to directly measure the magnetic field strength of the magnetizable material. In a second embodiment, a sensor winding is used to sense the magnetic field strength of the magnetizable material. The sensor winding is interconnected with an amplifier so that changes in flux can be sensed.

20 Claims, 2 Drawing Sheets

AUTOCLAVE CYCLE MONITOR FOR AUTOCLAVED INSTRUMENTS

BACKGROUND OF THE INVENTION

The present invention relates to an electronic autoclave cycle sensor. Instruments used in surgery must be cleaned and sterilized after each use to eliminate microorganisms and viruses to prevent infection. While many sterilization methods are used, the most effective, lowest cost, quickest and most available method is application of steam in an autoclave. However, an autoclave provides a hostile environment causing wear on surgical instruments that, over time, requires maintenance to avoid instrument failure.

Often, manufacturers set prescribed design goals for their instruments including warranting the minimum number of autoclave cycles that the instrument is designed to withstand. Accordingly, it is helpful for the user to know how many autoclave cycles his or her instruments have undergone so that appropriate maintenance can be scheduled. Additionally, manufacturers of instruments are interested in knowing whether an instrument has been subjected to a sufficient number of autoclave cycles so as to render the instrument warranty void.

U.S. Pat. No. 3,450,489 to Fay discloses a sterilization control means that includes a thermal responsive signal producing means enclosed within wrapped articles to be sterilized. The signal means produces and transmits a control signal from within the bundle which is used to control the sterilization operation to ensure thorough sterilization of the wrapped articles. Fay fails to teach or suggest any means for counting the number of cycles to which an instrument has been subjected nor does Fay teach or suggest any magnetic means to sense the number of autoclave cycles to which an instrument has been subjected.

U.S. Pat. No. 3,568,627 to Sellenger et al. discloses a combined record card and sterilization indicator including a portion of the record that changes colors to indicate that sterilization has taken place. Sellenger et al. fail to teach or suggest any magnetic means for counting the number of autoclave cycles to which an instrument has been subjected.

U.S. Pat. No. 4,235,842 to Thomas et al. discloses a temperature cycle indicating means for a sterilizer unit that is designed to count the number of cycles of sterilization to which contact lenses have been subjected. Thomas et al. fail to teach or suggest the use of magnetic means to perform such function.

U.S. Pat. No. 4,850,716 to Baker et al. discloses a remotely detectable sterilization monitor that detects conditions indicative of sterilization through the melting of compounds. Magnetic material of high permeability and low coercivity create two distinct magnetic states. When the magnetic material melts responsive to exposure to high temperature, magnetized material is released and moves away from its original location due to spring tension from adjacent magnetic material thereby decreasing the bias effect of the first-mentioned magnetic material. When interrogation is conducted by an external force field, this separation may be detected. The present invention differs from the teachings of Baker et al. as contemplating use of magnetic sensing means for sensing a magnetic field and, responsive thereto, signaling that a cycle of sterilization has taken place.

U.S. Pat. No. 5,313,935 to Kortenbach et al. discloses an apparatus for counting the number of times a surgical instrument has been used. Kortenbach et al. employ a bi-metallic element that moves responsive to temperature change to cause a ratchet wheel to be advanced through engagement by an inwardly extending tooth to advance an indicator to show that one sterilization cycle has taken place. Kortenbach et al. fail to teach or suggest the use of magnetic sensing means.

SUMMARY OF THE INVENTION

The present invention relates to an electronic autoclave cycle sensor. The invention records the number of thermal cycles to which an instrument has been subjected in a steam autoclave. Since surgical instruments are not supplied with power during autoclave sterilization, the inventive sensor is required to record the existence of a temperature change cycle passively, which event must be detectable through electrical reading and wherein the sensor must be electrically re-settable.

When a sterilization cycle has been completed, and the instrument is next energized in use, computer means comprising a microprocessor or microcontroller is employed to read the sensor and record the occurrence of a sterilization cycle.

Information as to the cumulative number of cycles through which the instrument has been subjected is stored in a nonvolatile memory means such as, for example, an EEPROM. This data is suitably displayed on a display panel and/or is read out to a service computer on a serial data port or over a modem to a factory service center.

When an unmagnetized ferromagnetic material is placed in a magnetic field, such as is the case when a current passes through a coil around the material, the flux density of the material rises. When the magnetic field is removed by stopping flow of the current, the flux density remains. This phenomenon is known as "permanent magnetism". If the temperature of the material is raised above a critical value called the "Curie temperature", the exchange coupling suddenly disappears and the material becomes simply "paramagnetic". Paramagnetic materials do not exhibit the properties of permanent magnetism and their flux density is zero in the absence of an external field. At temperatures near but below the Curie temperature, the effect is only partial causing a permanent magnet to lose some of its retained flux density.

In the present invention, the sensor means employed uses either the Curie temperature or a temperature near but below the Curie temperature of a ferromagnetic material by first magnetizing the material and then, later, checking its flux density to determine whether a thermal cycle has occurred. As should be understood from the above explanation, if the magnetized material has been exposed to a temperature at or near the Curie temperature, the magnetic flux density will fall and this fact can be sensed through energization of a magnetic sensor. After sensing and recordation of an autoclave sterilization cycle, the magnetic material is re-magnetized so that it is ready to be used to sense the next sterilization cycle.

In the preferred embodiment, the magnetic material employed has a relatively low Curie temperature so that its Curie temperature is reached or approached within the normal range of operating temperatures of an autoclave. An example of such a material is Nd—Fe—B alloy.

The present invention contemplates two possible sensor means for measuring the flux density of a magnetizable material. In a first embodiment, a Hall effect sensor is used to directly measure the magnetic field strength of the magnetizable material so that the user can determine whether the magnetic field strength has been reduced as would be the case should the material be exposed to the near Curie or Curie temperature thereof. In a second embodiment, a sensor winding is used to sense the magnetic field strength of the magnetizable material which can be made in a variety of shapes such as toroid shaped, similar to that used in magnetic core memory devices. The sensor winding is interconnected with an amplifier so that changes in flux can be sensed.

Accordingly, it is a first object of the present invention to provide an electronic autoclave cycle sensor.

It is a further object of the present invention to provide such a device wherein a Hall effect sensor is employed to sense changes in the magnetic field strength of a magnetizable material.

It is a still further object of the present invention to provide such a device, in another embodiment thereof, which employs a sensor winding in series with an amplifier to facilitate sensing of the magnetic field strength of a magnetizable material.

It is a still further object of the present invention to provide such a device wherein a non-volatile memory is employed to store data as to the number of cycles to which an instrument has been subjected.

These and other objects, aspects and features of the present invention will be better understood from the following detailed description of the preferred embodiments when read in conjunction with the appended drawing figures.

SPECIFIC DESCRIPTION OF THE PREFERRED EMBODIMENTS

Figure 1:
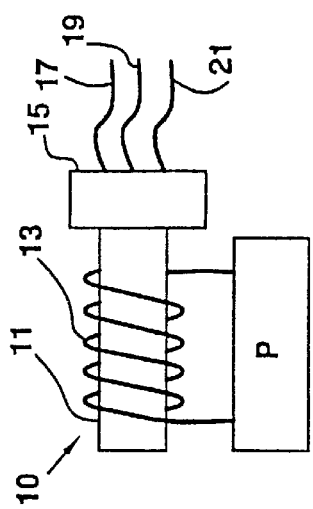
FIG. 1 shows a schematic representation of a first embodiment of the present invention employing a Hall effect sensor.

With reference to FIG. 1, a first embodiment of the present invention includes a sensor sub-circuit generally designated by the reference numeral 10 and including a ferromagnetic magnetizable material 11 surrounded by a coil 13, with the material 11 connected to a Hall effect sensor 15 that includes three wires; namely, a power wire 17, a ground wire 19, and a signal output wire 21. A source of power P controlled by a microcontroller 30 (FIGS. 3–4) is used to re-magnetize material 11.

Figure 3:
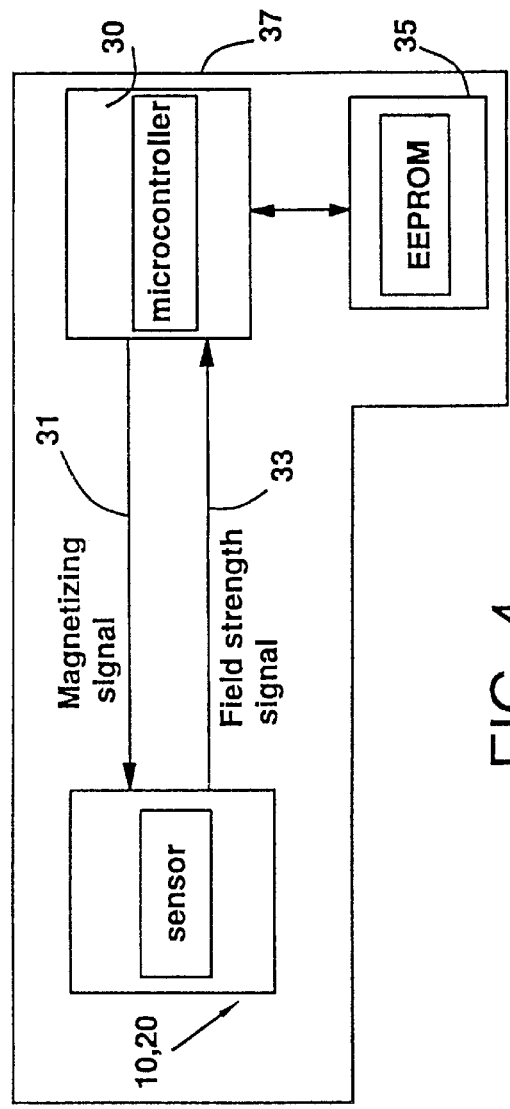
FIG. 3 shows a schematic representation of one construction of the present invention in either of the embodiments illustrated in FIGS. 1 and 2 where the entirety of the system is contained within a single housing.
Figure 4:
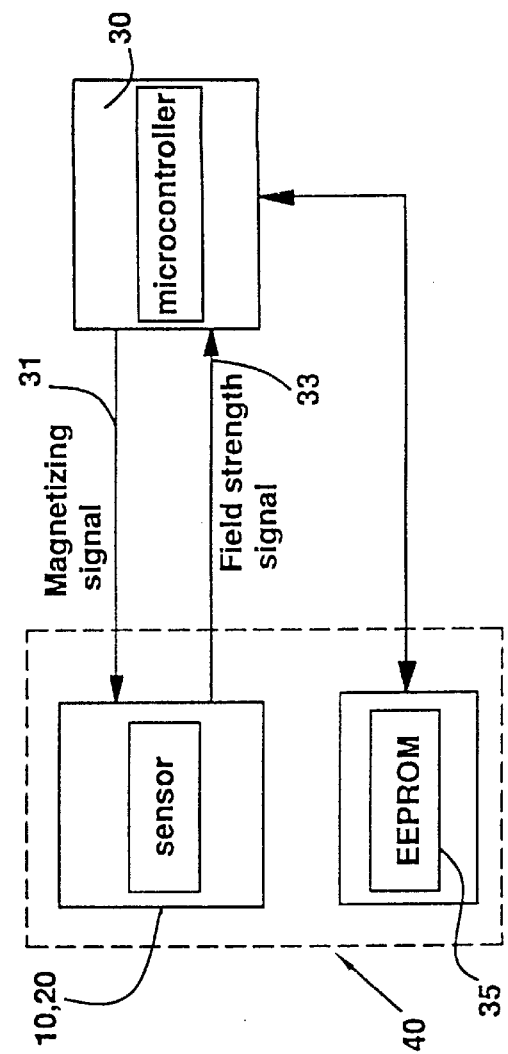
FIG. 4 shows a modification of the system illustrated in FIG. 3 wherein only the sensor sub-circuit and the memory portion are subjected to autoclaving.
Figure 2:
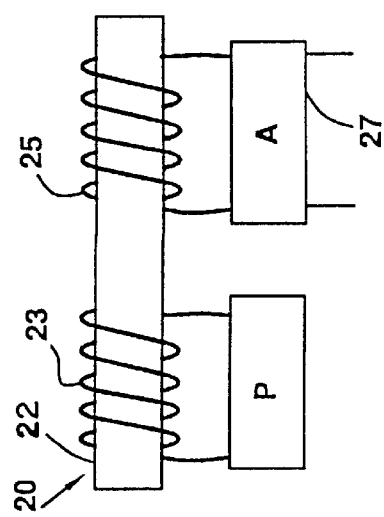
FIG. 2 shows a schematic representation of a second embodiment of the present invention employing a sensor winding.

With reference to FIG. 2, a second embodiment of the sensor sub-circuit 20 is seen to include a bar of ferromagnetic magnetizable material 22 surrounded by a magnetizing winding 23 and a sensor winding 25. The sensor winding 25 is interconnected into an amplifier 27 that supplies amplified signals to microcontroller 30 (FIGS. 3–4). Both the magnetizing winding 23 and the sensor winding 25 can consist of as little as a partial turn or length of wire. For example, in a core memory device a toroid shaped material is used and the sensor and magnetizing windings are simply a wire passed once through the toroid shaped material.

With reference to FIG. 3, the sensor sub-circuits 10, 20 are seen to be connected to a microcontroller 30 by conductors 31 and 33. Conductor 31 provides activation and de-activation signals for power source P. Conductor 33 conveys field strength signals from the sensor winding 25 (FIG. 2) or from the Hall effect sensor (FIG. 1) to the microcontroller 30 (FIGS. 3 and 4). The microcontroller 30 is connected to a non-volatile memory 35 such as, for example, an EEPROM. The reference numeral 37 refers to an outer housing wall designed to enclose all of the components illustrated in FIG. 3 into a single assembly designed to be attached to an instrument for which the number of autoclaving cycles is to be measured.

In the construction illustrated in FIG. 3, when the power is activated, the microcontroller 30 checks the state of the sensor 10 or 20 through the field strength signal line 33 and then records whether a formal cycle has been experienced by the sensor 10, 20. It is presumed that all of the elements depicted in FIG. 3 are built into the instrument that is periodically autoclaved in a non-electrically energized state and then is later connected to a power source such as a battery or an electrical outlet when it is to be operated. The microcontroller 30 checks the sensor whether it is the sensor sub-circuit 10 or 20 in the manner explained above, records data received, and then re-magnetizes the material 11 or 22 through the magnetizing signal line 31 and power source P.

FIG. 4 shows an alternative construction to the construction of FIG. 3 wherein an outer housing 40 encloses the sensor 10, 20 as well as the non-volatile memory 35 while the microcontroller 30 is connected externally to the housing 40 and, therefore, is not subjected to the autoclaving process. The construction illustrated in FIG. 4 has a longer expected lifetime since the microcontroller 30 is not subjected to the high extremes of temperature as would be the case in the construction illustrated in FIG. 3.

An example of a use of the construction illustrated in FIG. 4 would be where an endoscopic video camera head is to be autoclaved and then connected to a controller unit for use in a surgical operating room. In such a case, the microcontroller is located in the controller unit and only the sensor and EEPROM non-volatile memory reside in the autoclavable portion of the system.

Figure 6:
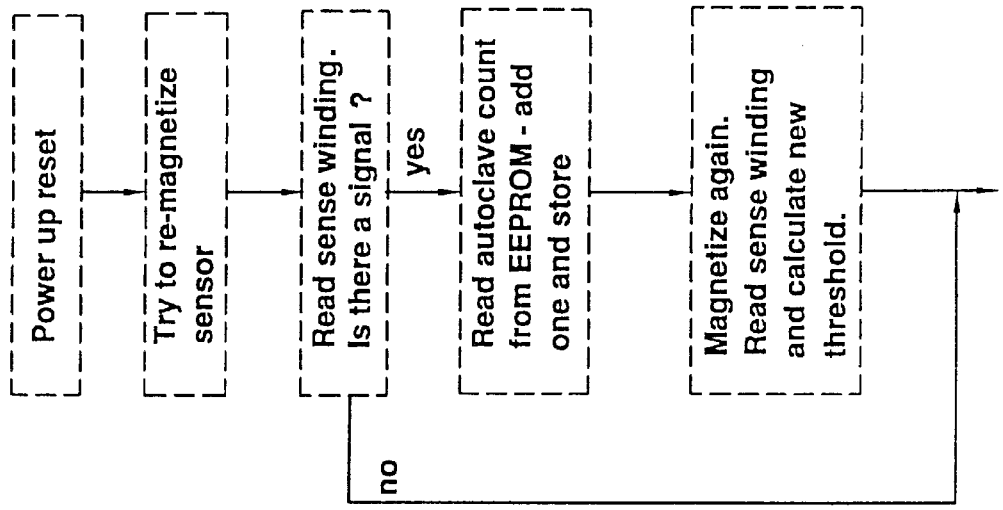
FIG. 6 shows a flowchart of the inventive system employing the sensor sub-circuit of FIG. 2.
Figure 5:
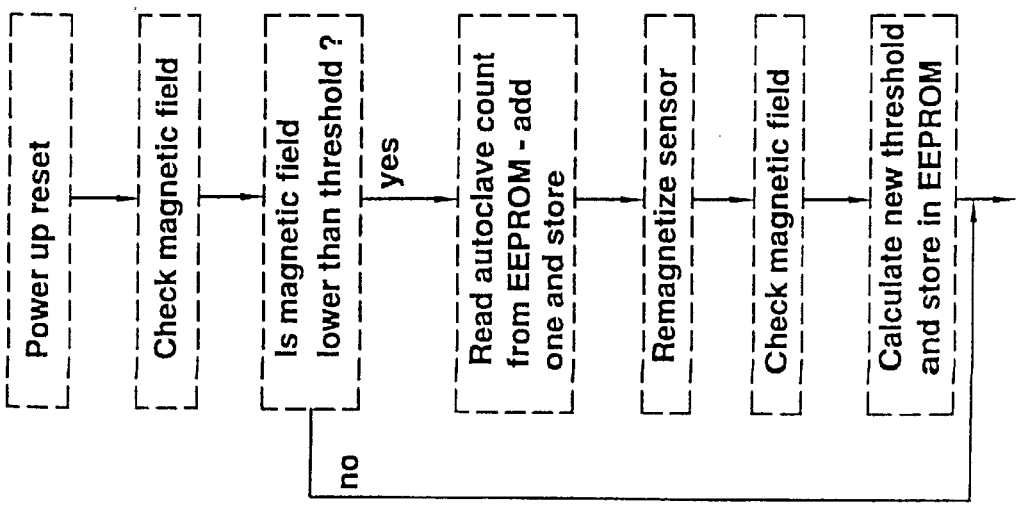
FIG. 5 shows a flowchart of the operation of the inventive system including the sensor of FIG. 1.

FIG. 5 shows a flowchart of the operation of the present invention where the sensor sub-circuit of FIG. 1 is employed. FIG. 6 shows a flowchart of the operation of the inventive system where the sensor sub-circuit illustrated in FIG. 2 is employed. in light of the disclosure set forth hereinabove, these flowcharts are self-explanatory. The flowcharts of FIGS. 5 and 6 describe the inventive method of counting autoclave cycles using either embodiment of sensor sub-circuit as illustrated in FIGS. 1 and 2.

Each of the sensor sub-circuits disclosed herein and particularly illustrated in FIGS. 1 and 2 uses the concept of the Curie temperature or near Curie temperature of a ferromagnetic magnetizable material to determine whether an autoclave cycle has been experienced. During each case, the ferromagnetic material is first magnetized and then, sometime later, the flux density thereof is checked to determine if a formal cycle has occurred. If the ferromagnetic material has been exposed to a temperature at or near the Curie temperature, the magnetic flux density will fall and this can be sensed by either of the sensor sub-circuits described in FIGS. 1 and 2. If the flux density of the material has fallen, the material is re-magnetized by passing a current through the coil 13 or 23. This action re-sets the sensor 10 or 20 so that it is in a proper condition to observe another cycle of autoclaving. As explained above, it is not necessary to reach the Curie temperature to facilitate noting of a change in flux density. Merely approaching the Curie temperature results in some lowering of the flux density which is detected.

Accordingly, an invention has been disclosed in terms of apparatus and method that fulfill each and every one of the objects of the invention as set forth hereinabove and provide a new and useful electronic autoclave cycle sensor and method of sensing autoclave cycles of great novelty and utility.

Of course, various changes, modifications and alterations in the teachings of the present invention may be contemplated by those skilled in the art without departing from the intended spirit and scope thereof.

As such, it is intended that the present invention only be limited by the terms of the appended claims.

What is claimed is:

1. A device for monitoring a number of cycles of autoclaving to which an instrument is subjected, comprising:
   a) a ferromagnetic magnetizable material member having a prescribed magnetic flux density, the magnetizable material attachable to an instrument;
   b) an electrical conductor winding around the magnetizable material member and connected to a source of electric power to re-magnetize the magnetizable material when the flux density of the magnetizable material has been reduced in an autoclave cycle;
   c) sensor means operatively associated with the magnetizable material member for measuring the magnetic flux density of the magnetizable material member;
   d) computer means for receiving signals from the sensor means when the magnetic flux density of the magnetizable material member has been reduced;
   e) the computer means including memory means for storing data received from the sensor means indicative of said number of cycles.

2. The device of claim 1, wherein the magnetizable material member is made of a material having a low Curie temperature.

3. The device of claim 2, wherein the magnetizable material comprises Nd—Fe—B alloy.

4. The device of claim 1, wherein the sensor means comprises a Hall effect sensor.

5. The device of claim 1, wherein the sensor means comprises a sensor coil.

6. The device of claim 5, further including an amplifier interposed between the sensor coil and computer means.

7. The device of claim 1, wherein the memory means comprises an EEPROM.

8. The device of claim 1, wherein the sensor means, computer means and memory means are contained in a single housing.

9. The device of claim 1, wherein the sensor means and memory means are contained in a single housing.

10. The device of claim 9, wherein the computer means is located exterior of said housing.

11. A device for monitoring a number of cycles of autoclaving to which an instrument is subjected, comprising:
    a) a ferromagnetic magnetizable material member having a prescribed magnetic flux density, a low Curie temperature and attachable to the instrument;
    b) an electrical conductor winding around the magnetizable material member and connected to a source of electric power to re-magnetize the magnetizable material when the flux density of the magnetizable material has been reduced in an autoclave cycle;
    c) sensor means operatively associated with the magnetizable material member for measuring the magnetic flux density of the magnetizable material member;
    d) computer means for receiving signals from said sensor means when the magnetic flux density of the magnetizable material member has been reduced;
    e) the computer means including memory means comprising an EEPROM for storing data received from the sensor means indicative of said number of cycles.

12. The device of claim 11, wherein the magnetizable material member comprises Nd—Fe—B alloy.

13. The device of claim 11, wherein the sensor means comprises a Hall effect sensor.

14. The device of claim 11, wherein the sensor means comprises a sensor coil.

15. The device of claim 14, further including an amplifier interposed between the sensor coil and computer means.

16. The device of claim 11, wherein the sensor means, computer means and memory means are contained in a single housing.

17. The device of claim 11, wherein the sensor means and memory means are contained in a single housing.

18. The device of claim 17, wherein the computer means is located exterior of the housing.

19. The device of claim 11, wherein the electrical conductor is wound about the ferromagnetic magnetizable material in the shape of a bar.

20. The device of claim 19, wherein the sensor means is attached to the magnetizable material in the shape of a bar.

* * * * *